(12) United States Patent
Bowman et al.

(10) Patent No.: US 9,044,508 B2
(45) Date of Patent: Jun. 2, 2015

(54) CONCENTRATED AQUEOUS AZALIDE FORMULATIONS

(71) Applicant: INSITE VISION CORPORATION, Alameda, CA (US)

(72) Inventors: Lyle M. Bowman, Pleasanton, CA (US); Sui Yen Eddie Hou, Foster City, CA (US); Tang Nguyen, Alameda, CA (US)

(73) Assignee: INSITE VISION CORPORATION, Pleasanton, CA (US)

( * ) Notice: Subject to any disclaimer, the term of this patent is extended or adjusted under 35 U.S.C. 154(b) by 0 days.

(21) Appl. No.: 13/843,267

(22) Filed: Mar. 15, 2013

(65) Prior Publication Data

US 2014/0274924 A1 Sep. 18, 2014

(51) Int. Cl.

| | | |
|---|---|---|
| *A61K 31/70* | (2006.01) | |
| *A61K 47/02* | (2006.01) | |
| *A61K 31/573* | (2006.01) | |
| *A61K 31/7052* | (2006.01) | |
| *A61K 9/00* | (2006.01) | |
| *A61K 47/10* | (2006.01) | |
| *A61K 47/32* | (2006.01) | |
| *A61K 47/36* | (2006.01) | |

(52) U.S. Cl.
CPC .............. *A61K 47/02* (2013.01); *A61K 31/573* (2013.01); *A61K 31/7052* (2013.01); *A61K 9/0048* (2013.01); *A61K 47/10* (2013.01); *A61K 47/32* (2013.01); *A61K 47/36* (2013.01)

(58) Field of Classification Search
CPC ........... A61K 31/7048; A61K 31/7052; A61K 31/573; A61K 47/36; A61K 9/0048
USPC .......................................................... 514/29
See application file for complete search history.

(56) References Cited

U.S. PATENT DOCUMENTS

| 4,136,250 | A | 1/1979 | Mueller et al. |
|---|---|---|---|
| 4,192,827 | A | 3/1980 | Mueller et al. |
| 5,223,493 | A | 6/1993 | Boltralik |
| 6,239,113 | B1 | 5/2001 | Dawson et al. |
| 6,277,829 | B1 | 8/2001 | Asero et al. |
| 6,378,526 | B1 | 4/2002 | Bowman et al. |
| 6,397,849 | B1 | 6/2002 | Bowman et al. |
| 6,514,945 | B1 | 2/2003 | Boettner |
| 6,569,443 | B1 | 5/2003 | Dawson et al. |
| 7,056,893 | B2 | 6/2006 | Roy et al. |
| 7,795,231 | B2 * | 9/2010 | Bowman et al. ................ 514/28 |
| 2006/0228394 | A1 | 10/2006 | Peyman |
| 2008/0161250 | A1 | 7/2008 | Dawson |
| 2009/0093449 | A1 | 4/2009 | Bowman et al. |
| 2010/0226997 | A1 * | 9/2010 | Bowman et al. .............. 424/501 |

OTHER PUBLICATIONS

Notification of Transmittal of the International Search Report and the Written Opinion of the International Searching Authority issued in International Application No. PCT/US2014/022084 dated Jul. 31, 2014.

* cited by examiner

*Primary Examiner* — Elli Peselev
(74) *Attorney, Agent, or Firm* — McDermott Will & Emery LLP

(57) ABSTRACT

Provided is concentrated aqueous azithromycin formulation from about from about 2%-20%, and a method of making a concentrated aqueous azithromycin formulation which includes preparing and sterilizing a first solution comprising a strong base to form a sterilized solution, dissolving the azithromycin in an aqueous solution comprising an acid consisting essentially of a strong acid, and adding the aqueous solution comprising the strong acid to the sterilized solution comprising the strong base. The strong acid has a pKa less than about −1.74 and the method is carried out without addition or use of a weak acid.

21 Claims, 1 Drawing Sheet

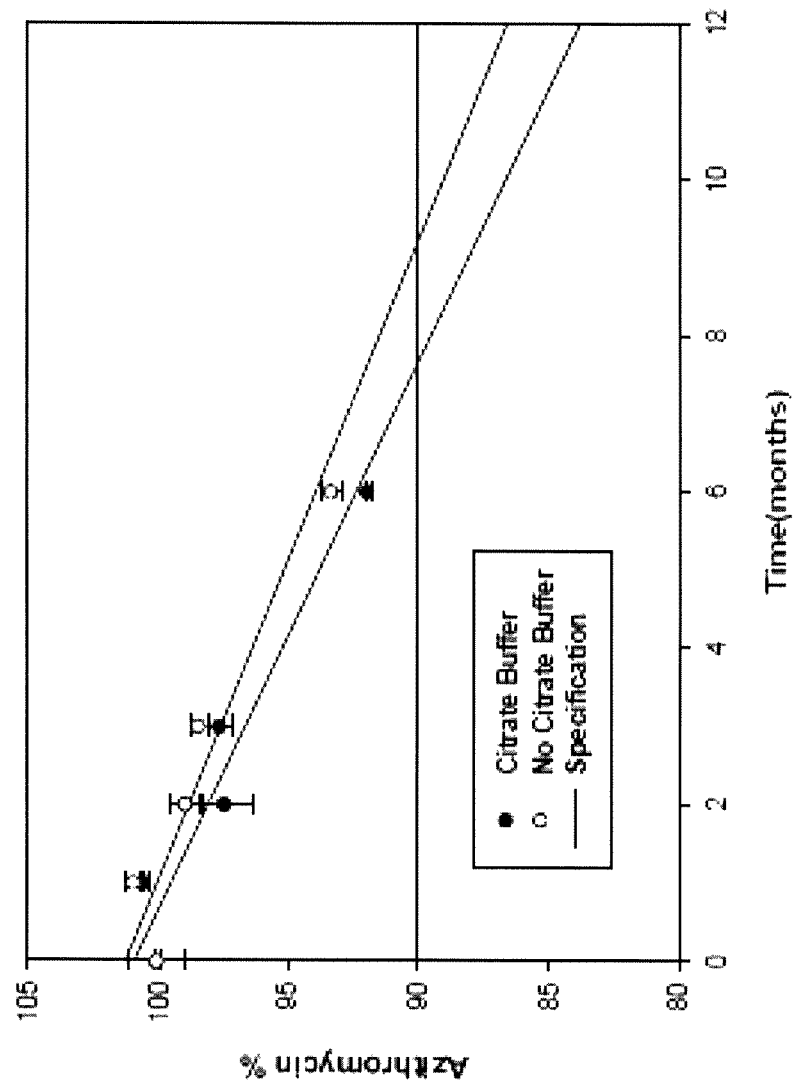

CONCENTRATED AQUEOUS AZALIDE FORMULATIONS

FIELD

The present disclosure relates to formulations of concentrated azalide antibiotics and methods for making and using them.

BACKGROUND

Compared to systemic administration, the simple and direct approach of topically applying a drug, such as an antibiotic, to the eye has several benefits, including the avoidance of side effects, bypassing the hepatic first pass, and reducing the likelihood of developing resistant strains of bacteria. However, for a variety of reasons, such as difficulty in delivering an effective amount of antibiotic to treat the infection, many antibiotics are not amenable or suitable for topical application to the eye or the tissue surrounding the eye, such as the eyelid.

U.S. Pat. No. 6,277,829 discloses a process for the preparation of an aqueous ophthalmic formulation containing azithromycin which comprises the ophthalmically acceptable polybasic phosphate, citric acid monohydrate, and azithromycin. However, these solutions which utilize phosphate buffer systems comprising phosphoric acid in combination with an external stabilizer, such as citric acid, can be irritating to the eye. Additionally, phosphate buffered system can promote fungus growth in the formulation.

As such there remains a need for stable concentrated yet well tolerated aqueous formulations of azalide antibiotics for topical application to the eye.

All documents scientific and patent, cited herein are incorporated by reference in their entirety.

SUMMARY

An aspect of the present disclosure provides a method of making a concentrated aqueous azithromycin formulation comprising from about 2% to 20% azithromycin, the method comprises steps of: preparing and sterilizing a first solution comprising a polymeric suspending agent the pH of which is adjusted with a strong base to form the first solution, dissolving the azithromycin in an aqueous solution comprising an acid consisting essentially of a strong acid to form a second solution, and adding the second solution comprising the strong acid to the first solution, wherein the strong acid has a pKa less than about −1.74 and the method is carried out without addition or use of a weak acid.

The strong acid may be hydrochloric acid and the strong base may be sodium hydroxide. The polymeric suspending agent may be a lightly crosslinked carboxy-containing polymer such as Noveon AA-1. The aqueous azithromycin formulation may further comprise an anti-inflammatory agent and the anti-inflammatory agent may be dexamethasone. The dexamethasone may have a concentration of about 0.1% per weight of the total concentrated aqueous azithromycin formulation. The aqueous solution may comprise a chitosan having a molecular weight from about 500 kDa to about 5,000 kDa in an amount from about 0.01% to about 1.0%. The concentrated aqueous azithromycin formulation is made in the absence of an acid having a pKa greater than about 3.0.

According to another embodiment, provided is a method of treating a condition of the eye comprising the steps of preparing a concentrated aqueous azithromycin formulation comprising from about 2% to 20% azithromycin, by sterilizing a first solution comprising a polymeric suspending agent the pH of which is adjusted with a strong base to form the first solution; dissolving the azithromycin in an aqueous solution comprising an acid consisting essentially of a strong acid to form a second solution; and adding the second solution comprising the strong acid to the first solution adjusted with the strong base, wherein the strong acid has a pKa less than about −1.74 and the method is carried out without addition or use of a weak acid; and applying the formulation to the eye and/or the tissue surround the eye in an amount effective to treat the eye.

The condition of the eye may be selected from blepharitis, blepharconjunctivies, meibomianitis, acute or chronic hordeolum, chalazion, dacryocystitis, dacryoadenities, acne rosacea, bacterial conjunctivitis, ophthalmia neonatorum, trachoma, corneal ulcers, superficial and interstitial keratitis, keratoconjunctivitis, foreign bodies, post operative infections, endophthalmitis, or infectious uveitis.

The formulation may be applied to the eye and/or the tissue surround the eye prior to an ocular surgical procedure.

According to another aspect, provided is a concentrated topical aqueous azalide antibiotic formulation comprising 2% to about 20% azithromycin and a polymeric agent, the formulation made by dissolving azithromycin in a strong acid and then adding the dissolved azithromycin to a sterilized solution comprising the polymeric suspending agent the pH of which is adjusted with a base, wherein the strong acid has a pKa less than about −1.74 and wherein the formulation is made in the absence of a weak acid.

Additional advantages of the present disclosure will become readily apparent to those skilled in this art from the following detailed description, wherein only the one embodiment is shown and described, simply by way of illustration of the best mode contemplated. As will be realized, the inventive subject matter is capable of other and different embodiments, and its several details are capable of modifications in various obvious respects. The present subject matter may be practiced without some or all of these specific details. In other instances, well known process operations have not been described in detail to avoid unnecessarily obscuring the present disclosure. Accordingly, the description is to be regarded as illustrative in nature, and not as restrictive.

BRIEF DESCRIPTION OF THE DRAWING

FIG. 1 shows the stability over time of the present formulation versus a formulation made with citric acid and citrate.

DETAILED DESCRIPTION

Azalides are a known subclass of macrolide antibiotics. The azalide antibiotics of the present disclosure are represented by formula (I) and pharmaceutically acceptable salts thereof.

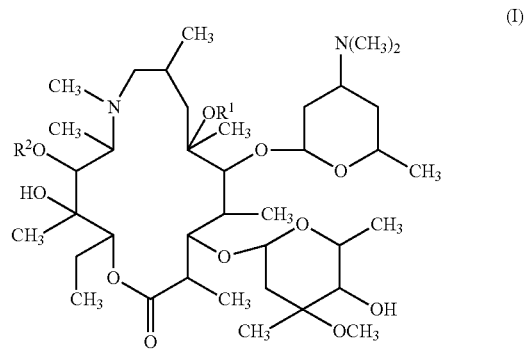

$R^1$ and $R^2$ each independently represent a hydrogen atom or methyl group. At least one of $R^1$ and $R^2$ is a hydrogen atom. Azithromycin, the common name for N-methyl-1'-aza-10-deoxo-10-dihydroerythromycin, corresponds to the compound of formula (I) where both $R^1$ and $R^2$ are hydrogen atoms. Azithromycin was disclosed in U.S. Pat. Nos. 4,474,768 and 4,517,359. In particular, the monohydrate form of azithromycin is especially contemplated for use in formulations of the present disclosure, although other forms are also suitable.

According to an aspect of the disclosure there is provided a process of preparing a stable concentrated aqueous azalide antibiotic formulation without the use of an external stabilizer, such as a weak acid, for example citric acid, fumaric acid, malic acid, tartaric acid, acetic acid which will buffer the solution to prevent degradation of the azithromycin molecule. In other words, the present formulation is made in a strong acid and no weak acid (or other external stabilizer) is added to the composition to stabilize the azithromycin.

The process generally involves dissolving an azalide antibiotic in a strongly acidic aqueous solution without the use of a stabilizer such as a weak acid, and then adding to the dissolved azalide antibiotic solution, a suspending agent, the pH of which is adjusted using a strong base. The final pH of the formulation may be adjusted to about 6.0 to about 7.0, or in some embodiments, from about 6.0 to about 6.6, about 6.2 to about 6.4, 6.25 to 6.35, or other embodiments to a pH of about 6.3.

"Strong acid" as used herein refers to an acid that dissociates completely in an aqueous solution (not in the case of sulfuric acid as it is diprotic), or in other terms, having a pKa of less than about −1.74. This generally means that in aqueous solution at standard temperature and pressure, the concentration of hydronium ions is equal to the concentration of strong acid introduced to the solution. In some embodiments, the strong acids include but are not limited to hydrochloric, sulfuric, acetic, nitric, and perchloric acids. An embodiment uses hydrochloric acid as the strong acid.

"Strong base" as used herein refers to a basic chemical compound that is able to deprotonate very weak acids in an acid-base reaction. Such compounds may have a pKa of more than about 13. Common examples of strong bases are the hydroxides of alkali metals and alkaline earth metals like NaOH. Certain strong bases are even able to deprotonate very weakly acidic C—H groups in the absence of water. Strong bases include but are not limited to potassium hydroxide, barium hydroxide, cesium hydroxide, sodium hydroxide, strontium hydroxide, lithium hydroxide and rubidium hydroxide. An embodiment uses NaOH as the strong base.

The term "weak acid" as used herein refers to an acid having a pKa above about 2.0. or in some embodiments the weak acid has a pKa above 3.0. Examples of such weak acids are: citric acid and sodium citrate. Such weak acids are examples of an external stabilizer. The term "external stabilizer" is used herein to denote any compound added to the azithromycin during it's dissolution with a strong acid in order to stabilize azithromycin in the presence of the strong acid.

Previously, azithromycin antibiotics had been discovered to have a maximum stability over a pH interval of about 6.0 to about 7.0, with a maximum stability at a pH of about 6.3 (See U.S. Pat. No. 7,056,893). Given this teaching, the skilled artisan would seek to avoid pH ranges below 6 and above 7 when formulating aqueous formulations of azalide antibiotics. However, it was surprisingly discovered by Applicant that concentrated aqueous azalide antibiotic formulations can be made by dissolving the azalide antibiotic in a strong acid (pKa less than about −1.74) without the use of an external stabilizer such as a weak acid and then bringing the pH to a range of about 6.0 to about 7.0 with a base. Notwithstanding concerns that the strongly acidic conditions would cause degradation of the azalide antibiotic, it was found that dissolving azalide antibiotic in a strong acid and subsequent pH adjustment did not have a deteriorative effect on the azalide antibiotic.

Moreover, it was further surprisingly discovered that concentrated aqueous azalide antibiotic formulations made in the absence of a weak acid stabilizer have improved stability in comparison to formulations made using the weak acid stabilizer. Thus, the present disclosure provides a more stable formulation of concentrated azithromycin.

The term "concentrated" aqueous azalide antibiotic formulation refers to an aqueous solution of an azalide antibiotic having a concentration of about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20% about 21%, about 22%, about 23%, about 24%, about 25%, about 26% about 27%, about 28%, about 29% or about 30%. In certain embodiments the concentrated formulation is about 1% to about 30%, 2% to about 25%, or about 2% to about 20%. In some embodiments, the azalide antibiotic concentration is about 2% to about 8%.

Although azithromycin can reach many tissues by oral administration, it has been discovered that azalide antibiotics, in general, and azithromycin, in particular, are amenable to topical administration. U.S. Pat. Nos. 6,239,113, 6,569,443, 7,056,893, all of which are incorporated by reference in their entirety.

"Topical administration" refers to a route of administration which is the path by which the azalide antibiotic is brought into contact with the body. In topical administration the effect of the azalide antibiotic is local and the composition is usually applied directly where its therapeutic action is desired. Topical application is application directly to the eye, the eye lid, or other tissue surrounding the eye.

In certain embodiments, the formulations may be formulated as drops, sprays, ointments, creams, lotions, gels, emulsions or other aqueous solutions or dispersions. The primary vehicle may be water or a biocompatible solvent that is substantially neutral or that has been rendered substantially neutral. The liquid vehicle can include other materials, such as alcohols, glycerin, polyethylene glycol, and mineral oils with various emulsifiers or dispersing agents as known in the art to obtain the desired pH, consistency and viscosity. In a further embodiment, the composition is an irrigating solution for use in a process of irrigating an ocular surgical site.

The amount of azalide antibiotic topically supplied is effective to treat or prevent infection in the eye. This means that the conditions of application result in a retardation or suppression of the infection. Typically at least about $MIC_{90}$ for the targeted bacteria or parasite is delivered to the target tissue by the topical application of an effective amount. More concretely, the concentration within the tissue is desired to be at least about 1 µg/g, in certain embodiments at least about 10 µg/g, such as at least about 20 µg/g. Delivery of formulations as a depot will advantageously maintain the concentration of the azalide antibiotic in the affected eye at or above the $MIC_{90}$ for a period of at least about 2 hours, in some embodiments at least about 4 hours, in other embodiments at least about 8 hours, in other embodiments at least about 12 hours and some embodiments at least 18 hours.

Where a series of applications are typically employed in a topical administration dosing regimen, it is possible that one or more of the earlier applications will not achieve an effective concentration in the eye but that a later application in the regimen will achieve an effective concentration. This is contemplated as being within the scope of topically applying an azalide antibiotic in an effective amount.

The concentration of azalide antibiotic depends upon the dosage form, the release rate, the dosing regimen, and type of infection. Generally speaking, the concentration is from about 2% to about 12.0% although it is possible to prepare and utilize formulations with higher concentrations of azalide antibiotics such as 15%, 20%, 25% or even about 30%. In one embodiment, the concentration is about 2% to about 20%. In another embodiment, the concentration is about 2% to about 10%. In another embodiment, the concentration is about 2% to about 5%. In another embodiment, the concentration is about 2% to about 3%. In another embodiment, the concentration is about 2% to about 2.5%.

Azalide antibiotic formulations suitable for topical administration to the eye may include one or more "pharmaceutically acceptable carriers," such as for example an ophthalmically acceptable carrier. Typically the pharmaceutically acceptable carriers are aqueous-based solution or suspension. Generally, azalide antibiotics are poorly soluble in water. However, the methods disclosed herein overcome this problem and allow for the preparation of concentrated azalide antibiotic formulations.

In some embodiments, the aqueous formulations (solutions or suspensions) use water that has no physiologically harmful constituents. Typically, purified or deionized water is used.

The formulations of the present disclosure are suitable for topical ophthalmic administration, including both ointments and suspensions, and are formulated to have a viscosity that is suited for the selected route of administration. Viscosity enhancing agents that may be used in the present formulations include, for example, polyvinyl alcohol, polyvinyl pyrrolidone, povidone, polyethylene glycol, Carbomer 940/934P, methyl cellulose, hydroxypropyl methylcellulose, hydroxyethyl cellulose, carboxymethyl cellulose.

The azalide antibiotic formulations containing aqueous polymeric suspensions may be formulated so that they retain the same or substantially the same viscosity that they had prior to administration to the tissue. Alternatively, in certain embodiments, they may be formulated so that there is increased gelation upon contact with the eye or tears.

The osmotic pressure ($\pi$) of the aqueous compositions of this disclosure is generally from about 10 milliosmolar (mOsM) to about 400 mOsM. In certain embodiments, about 260 to about 340 mOsM and in some embodiments about 280 to about 320 or about 300 mOsM. If necessary, the osmotic pressure can be adjusted by using appropriate amounts of physiologically acceptable salts or excipients. Sodium chloride may be used to approximate physiologic fluid, and amounts of sodium chloride from about 0.01% to about 0.9% by weight, and in certain embodiments from about 0.1% to about 0.9% by weight, and in other embodiments about 0.2% to about 0.5% by weight based on the total weight of the composition, are used.

The solubility of the components of the present formulations may also be enhanced by a surfactant or other appropriate co-solvent in the composition or solubility enhancing agents like cyclodextrins such as hydroxypropyl, hydroxyethyl, glucosyl, maltosyl and maltotriosyl derivatives of alpha-, beta-, and gamma-cyclodextrin. One such solubility enhancer as used in certain embodiments is hydroxypropyl-beta cyclodextrin (HPBC). In one embodiment, the composition comprises 0.1% to 20% hydroxypropyl-beta-cyclodextrin, in other embodiments 1% to 15% hydroxypropyl-beta-cyclodextrin, and certain embodiments from 2.5% to 10% hydroxypropyl-beta-cyclodextrin. Co-solvents include polysorbates (for example, polysorbate 20, 60, and 80), polyoxyethylene/polyoxypropylene surfactants (e.g., Pluronic F-68, F 84 and P-103), cyclodextrin, fatty-acid glycerol-polyethylene glycol esters, other solubilizing agents such as Octoxynol 40, Tyloxapol and Pluronics, or other agents known to those skilled in the art and mixtures thereof. The amount of solubility enhancer used will depend on the amount of azalide antibiotic in the composition, with more solubility enhancer used for greater amounts of azalides. Typically solubility enhancers are employed at a level of from 0.01% to 20% by weight depending on the ingredient. In certain embodiments, the ranges are 1% to 5% or 0.1% to 2%. Wetting agents include polyvinyl pyrolidone, polyvinyl alcohol, and polyethylene glycol. The solubilizing agents may help keep the other components of the topical composition in solution, including the azalide antibiotic in solution. The wetting agent helps the formulation to spread over the tissue.

If necessary, free divalent metal ions may be removed from the solution by using appropriate amounts of a chelating agent. EDTA disodium is used in certain embodiments to remove excess free metal ions. In addition to EDTA other chelating agents as Dequest 2060 may also be employed.

The formulations of the present disclosure may contain one or more of the following: surfactants, adjuvants including additional medicaments, antioxidants, tonicity adjusters, preservatives, thickeners or viscosity modifiers, and the like. Additives in the formulation may include sodium chloride, EDTA (disodium edetate), and/or BAK (benzalkonium chloride), methyl paraben, propyl paraben, chlorhexidine, and sodium perborate. Suitable preservatives also include: polyquaternium-1, thimerosal, chlorobutanol, methyl paraben, propyl paraben, phenylethyl alcohol, sorbic acid, or other agents known to those skilled in the art. Typically such preservatives are employed at a level of from 0.001% to 1.0% by weight.

The formulations may also advantageously employ one or more antioxidants. Useful antioxidants include, but are not limited to sodium bisulfate, butylated hydroxy toluene (BHT), thiourea, and sodium formaldehyde sulfoxylate.

The formulations may also achieve a sufficiently high tissue concentration with a minimum number of doses so that a simple dosing regimen can be used to treat or prevent bacterial or parasitic infections. To this end, according to certain embodiments, a technique is used that involves forming or supplying a depot of azalide antibiotic in contact with the eye or tissue surrounding the eye. A depot refers to a source of azalide antibiotic that is not rapidly removed by tears. This allows for continued, sustained high concentrations of azalide antibiotic to be present in the fluid on the surfaces of the eye tissue by a single application. In general, it is believed that absorption is dependent on both the dissolved drug concentration and the contact duration of the external tissue with the drug-containing fluid. As the drug is removed by clearance of the fluid and/or absorption into the tissue, more drug is provided, e.g. dissolved, into the replenished fluid from the depot.

Accordingly, the use of a depot more easily facilitates loading of the tissue in view of the typically slow and low penetration rate of the generally or poorly soluble azalide antibiotics. The depot, which retains a bolus of concentrated drug, can effectively slowly "pump" the azalide antibiotic into the tissue. As the azalide antibiotic penetrates the eye tissue, it is accumulated therein and not readily removed due to its long half-life. As more azalide antibiotic is "pumped" in, the tissue concentration increases and the minimum inhibitory concentration threshold is eventually reached or exceeded, thereby loading the tissue with azalide antibiotic. By significantly exceeding the $MIC_{50}$, or in some embodiments, exceeding the $MIC_{90}$ level, provided the toxicity limit is not exceeded, a therapeutically effective concentration will remain active in the tissue for an extended period of time due to the low clearance rate of the azalide antibiotic from the tissue. Thus, depending on the depot, one or two applications may provide a complete dosing regimen. Indeed, such a simple dosing regimen may provide a 6 to 14 day treatment concentration within the ocular tissue. A dosing regimen according to certain embodiments involves one to two doses per day over a one to three day period. In another embodiment, one or two doses in a single day, to provide in vivo at least a 6 day treatment and more typically a 6 to 14 day treatment.

A depot can take a variety of forms so long as the azalide antibiotic can be provided in sufficient concentration levels therein and is releasable therefrom, and that the depot is not readily removed from the tissue. A depot generally remains for at least about 30 minutes after administration, in some embodiments at least 2 hours, or at least 4 hours. The term "remains" means that neither the depot composition nor the azalide antibiotic is exhausted or cleared from the tissue prior to the indicated time. In some embodiments, the depot can remain for up to eight hours or more. Typical ophthalmic depot forms include aqueous polymeric suspensions, ointments, and solid inserts. In certain embodiments, polymeric suspensions are used.

According to certain embodiments, a form of the azalide formulations for administration of azalide antibiotics to the ocular tissues is an aqueous polymeric suspension. Here, at least one of the azalide antibiotic or the polymeric suspending agent is suspended in an aqueous medium having the properties as described above. The azalide antibiotic may be in suspension, although in the pH ranges according to certain embodiments, the azalide antibiotic will be in solution (water soluble), or both in solution and in suspension. It is possible for significant amounts of the azalide antibiotic to be present in suspension. The polymeric suspending agent may be in suspension (i.e. water insoluble and/or water swellable), although water soluble suspending agents are also suitable for use with a suspension of the azalide antibiotic. The suspending agent serves to provide stability to the suspension and to increase the residence time of the dosage form on the tissue. It can also enhance the sustained release of the drug in terms of both longer release times and a more uniform release profile.

Examples of polymeric suspending agents include dextrans, polyethylene glycols, polyvinylpyrolidone, polysaccharide gels, Gelrite™, cellulosic polymers like hydroxypropyl methylcellulose, and carboxy-containing polymers such as polymers or copolymers of acrylic acid, as well as other polymeric demulcents. According to one embodiment, the polymeric suspending agent is a water swellable, water insoluble polymer, especially a lightly crosslinked carboxy-containing polymer.

Crosslinked carboxy-containing polymers used in practicing the present subject matter are, in general, well known in the art. In one embodiment such polymers may be prepared from at least about 90%. In certain embodiments, from about 95% to about 99.9% by weight, based on the total weight of monomers present, of one or more carboxy-containing monoethylenically unsaturated monomers (also occasionally referred to herein as carboxy-vinyl polymers). According to certain embodiments, acrylic acid is the carboxy-containing monoethylenically unsaturated monomer, but other unsaturated, polymerizable carboxy-containing monomers, such as methacrylic acid, ethacrylic acid, β-methylacrylic acid (crotonic acid), cis-α-methylcrotonic acid (angelic acid), trans-α-methylcrotonic acid (tiglic acid), α-butylcrotonic acid, α-phenylacrylic acid, α-benzylacrylic acid, α-cyclohexylacrylic acid, β-phenylacrylic acid (cinnamic acid), coumaric acid (o-hydroxycinnamic acid), umbellic acid (p-hydroxycoumaric acid), and the like can be used in addition to or instead of acrylic acid.

Such polymers may be crosslinked by a polyfunctional crosslinking agent, such as a difunctional crosslinking agent. The amount of crosslinking should be sufficient to form insoluble polymer particles, but not so great as to unduly interfere with sustained release of the azalide antibiotic. Typically the polymers are only lightly crosslinked. In certain embodiments, the crosslinking agent is contained in an amount of from about 0.01% to about 5%, in some embodiments, from about 0.1% to about 5.0%, and in certain embodiments, from about 0.2% to about 1%, based on the total weight of monomers present. Included among such crosslinking agents are non-polyalkenyl polyether difunctional crosslinking monomers such as divinyl glycol; 2,3-dihydroxyhexa-1,5-diene; 2,5-dimethyl-1,5-hexadiene; divinylbenzene; N,N-diallylacrylamide; N,N-diallylmethacrylamide and the like. Also included are polyalkenyl polyether crosslinking agents containing two or more alkenyl ether groupings per molecule, such as alkenyl ether groupings containing terminal $H_2C=C<$ groups, prepared by etherifying a polyhydric alcohol containing at least four carbon atoms and at least three hydroxyl groups with an alkenyl halide such as allyl bromide or the like, e.g., polyallyl sucrose, polyallyl pentaerythritol, or the like; see, e.g., Brown U.S. Pat. No. 2,798,053, the entire contents of which are incorporated herein by reference. Diolefinic non-hydrophilic macromeric crosslinking agents having molecular weights of from about 400 to about 8,000, such as insoluble di- and polyacrylates and methacrylates of diols and polyols, diisocyanate-hydroxyalkyl acrylate or methacrylate reaction products of isocyanate terminated prepolymers derived from polyester diols, polyether diols or polysiloxane diols with hydroxyalkylmethacrylates, and the like, can also be used as the crosslinking agents; see Mueller et al. U.S. Pat. Nos. 4,192,827 and 4,136,250, the entire contents of each patent being incorporated herein by reference.

The crosslinked carboxy-vinyl polymers may be made from a carboxy-vinyl monomer or monomers as the sole monoethylenically unsaturated monomer present, together with a crosslinking agent or agents. In some embodiments, the polymers are ones in which up to about 40%, or from about 0% to about 20% by weight, of the carboxy-containing monoethylenically unsaturated monomer or monomers has been replaced by one or more non-carboxyl-containing monoethylenically unsaturated monomer or monomers containing only physiologically and ophthalmically innocuous substituents, including acrylic and methacrylic acid esters such as methyl methacrylate, ethyl acrylate, butyl acrylate, 2-ethylhexylacrylate, octyl methacrylate, 2-hydroxyethylmethacrylate, 3-hydroxypropylacrylate, and the like, vinyl acetate, N-vinylpyrrolidone, and the like; see Mueller et al. U.S. Pat. No. 4,548,990 for a more extensive listing of such additional monoethylenically unsaturated monomers.

In some embodiments, polymers are lightly crosslinked acrylic acid polymers wherein the crosslinking monomer is 2,3-dihydroxyhexa-1,5-diene or 2,3-dimethylhexa-1,5-diene. In certain embodiments, commercially available polymers include polycarbophil (Noveon AA-1) and Carbopol™. Certain embodiments use a carboxy-containing polymer system known by the tradename DuraSite®, containing polycarbophil, which is a sustained release topical delivery system is used in the aqueous polymeric suspension composition of the present disclosure.

The crosslinked carboxy-vinyl polymers used in practicing the present subject matter and may be prepared by suspension or emulsion polymerizing the monomers, using conventional free radical polymerization catalysts, to a dry particle size of not more than about 25 μm in equivalent spherical diameter; i.e., to provide dry polymer particles ranging in size from about 1 to about 25 μm, or from about 3 to about 20 μm, and in some embodiments, 1 μm to 10 μm in equivalent spherical diameter. In general, such polymers will have a molecular weight which has been variously reported as being from about 250,000 to about 4,000,000, and from 3,000,000,000 to 4,000,000,000. Using polymer particles that were obtained by mechanically milling larger polymer particles to this size is avoided.

In an embodiment, the particles of crosslinked carboxy-vinyl polymer are monodisperse, meaning that they have a dry particle size distribution such that at least 80% of the particles fall within a 10 μm band of major particle size distribution. In certain embodiments, at least 90%, in some embodiments, at least 95%, of the particles fall within a 10 μm band of major particle size distribution. Also, a monodisperse particle size means that there is no more than 20%, in some embodiments no more than 10%, and in other embodiments no more than 5% particles of a size below 1 μm. The use of monodispersed particles will give maximum viscosity and an increased eye residence time of the ophthalmic medicament delivery system for a given particle size. Monodisperse particles having a dry particle size of 10 μm and below are used in certain embodiments. Good particle packing is aided by a narrow particle size distribution.

The aqueous polymeric suspension normally contains azalide antibiotics in an amount from about 0.05% to about 25%, in certain embodiments about 0.1% to about 20%, in some embodiments about 0.5% to about 15%, in some embodiments about 1% to about 12%, in certain embodiments about 2% to about 10.0%, and polymeric suspending agent in an amount from about 0.05% to about 10%, in certain embodiments about 0.1% to about 5% and in some embodiments from about 0.1% to about 1.0% polymeric suspending agent. In the case of the above described water insoluble, water-swellable crosslinked carboxy-vinyl polymer, another embodiments uses the polymeric suspending agent in an amount from about 0.5% to about 2.0%, in certain embodiments from about 0.5% to about 1.2%, and in certain embodiments from about 0.5% to about 1.0%, based on the weight of the composition. Although referred to in the singular, it should be understood that one or more species of polymeric suspending agent, such as the crosslinked carboxy-containing polymer, can be used with the total amount falling within the stated ranges. In one embodiment, the composition contains about 0.5% to about 1.0% of the polymeric suspending agent such as Noveon AA-1(polycarbophil).

In one embodiment, the amount of insoluble lightly crosslinked carboxy-vinyl polymer particles, the pH, and the osmolality can be correlated with each other and with the degree of crosslinking to give a composition having a viscosity in the range of from about 50 to about 100,000 centipoises, and in certain embodiments from about 1,000 to about 30,000 or about 1,000 to about 10,000 centipoises, as measured at room temperature (about 25° C.) using a Brookfield Digital LVT Viscometer equipped with a number 25 spindle and a 13R small sample adapter at 12 rpm (Brookfield Engineering Laboratories Inc.; Middleboro, Mass.). Alternatively, when the viscosity is within the range of 500 to 5000 centipoises, it may be determined by a Brookfield Model DV-11+, choosing a number cp-52 spindle at 6 rpm.

When water soluble polymers are used as the suspending agent, such as hydroxypropyl methylcellulose, the viscosity will typically be about 10 to about 400 centipoises, more typically about 10 to about 200 centipoises or about 10 to about 25 centipoises.

In the aqueous solution, chitosan may be present in an amount ranging from about 0.01% to about 1.0% when using a cationic polymer having a molecular weight ranging from about 50 kDa to about 100 kDa. The amount of cationic polymer or chitosan can be any amount in between, including about 0.01%, 0.025%, 0.05%. 0.075%, 0.10%, 0.15%, 0.20%, 0.25%, 0.30%, 0.35%, 0.40%, 0.45%, 0.5%, 0.75% and 1.0% and any amount in between these values. When using higher molecular weight cationic polymers, such as in a range from about 500 to about 3,000 kDa, the amount of cationic polymer necessary to achieve favorable viscosities can be substantially reduced. For example, the amount of 500 kDa to about 5,000 kDa chitosan can be in a range from about 0.01% and 0.5%, or any amount in between including, for example, 0.01%, 0.015%, 0.020%, 0.025%, 0.030%, 0.035%, 0.040%, 0.045%, 0.05%, 0.1%, 0.15%, 0.20%, 0.25%, 0.30%, 0.35%, 0.40%, 0.45%, 0.50%, 0.75% and 1.0%.

A further aspect involves the use of additional medicaments in combination with the azalide antibiotic. A composition comprising a concentrated azalide antibiotic, an additional medicament, and a pharmaceutically acceptable carrier can advantageously simplify administration and allow for treating or preventing multiple conditions or symptoms simultaneously. The "additional medicaments," which can be present in any of the compositional forms described herein including fluid and solid forms, are pharmaceutically active compounds having efficacy in topical applications and which are compatible with an azalide antibiotic and with the eye. Typically, the additional medicaments include other antibiotics (an antibiotic that is different than an azalide antibiotic), antivirals, antifungals, anesthetics, anti-inflammatory agents, including steroidal and non-steroidal anti-inflammatories, and anti-allergic agents.

Examples of suitable medicaments include aminoglycosides such as amikacin, gentamycin, tobramycin, streptomycin, netilmycin, and kanamycin; fluoroquinolones such as gatifloxacin, moxifloxacin, ciprofloxacin, norfloxacin, ofloxacin, trovafloxacin, lomefloxacin, levofloxacin, and telithromycin, enoxacin; naphthyridine; sulfonamides; polymyxin; chloramphenicol; neomycin; paramomomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; comolyn; lodoxamide; levocabastin; naphazoling; antazoline; and pheniramimane. These other medicaments are generally present in a pharmaceutically effective amount as is understood by workers of ordinary skill in the art. These amounts are generally within the range of from about 0.01 to 5%, more typically 0.1 to 2%, for fluid formulations and from 0.5 to 50% for solid dosage forms.

The steroidal anti-inflammatory agents of the present disclosure include glucocorticoids, such as dexamethasone, loteprednol, rimexolone, prednisolone, prednisolone acetate, difluprednate, fluticasone propionate, busesonide, triamcinolone, beclomethasone, mometasone furoate, fluorometholone, and hydrocortisone. Dexamethasone derivatives such as U.S. Pat. No. 5,223,493, herein incorporated by reference, may also be used. Particular compounds include "21-ether derivatives of dexamethasone", such as a 21-benzyl ether derivatives of dexamethasone."

According to certain embodiments, the non-steroidal anti-inflammatory agents are: diclofenac, flurbiprofen, ketorolac, and suprofen. Other non-steroidal anti-inflammatory agents useable in the present disclosure include: prostaglandin H synthetase inhibitors (Cox I or Cox II), also referred to as cyclooxygenase type I and type II inhibitors, such as nepafenac, amfenac, indomethacin, naproxen, ibuprofen, bromfenac, ketoprofen, meclofenamate, piroxicam, sulindac, mefanamic acid, diflusinal, oxaprozin, tolmetin, fenoprofen, benoxaprofen, nabumetome, etodolac, phenylbutazone, aspirin, oxyphenbutazone, NCX-4016, HCT-1026, NCX-284, NCX-456, tenoxicam and carprofen; cyclooxygenase type II selective inhibitors, such as NS-398, vioxx, celecoxib, P54, etodolac, L-804600 and S-33516; PAF antagonists, such as SR-27417, A-137491, ABT-299, apafant, bepafant, minopafant, E-6123, BN-50727, nupafant and modipafant; PDE IV inhibitors, such as ariflo, torbafylline, rolipram, filaminast, piclamilast, cipamfylline, CG-1088, V-11294A, CT-2820, PD-168787, CP-293121, DWP-205297, CP-220629, SH-636, BAY-19-8004, and roflumilast; inhibitors of cytokine production, such as inhibitors of the NFkB transcription factor; or other anti-inflammatory agents known to those skilled in the art.

The concentrations of the anti-inflammatory agents contained in the formulations vary based on the agent or agents selected and the type of inflammation being treated. The concentrations will be sufficient to reduce inflammation in the eye following topical application of the formulations. Such an amount is referred to herein as "an anti-inflammatory effective amount". The formulations of the present disclosure may contain one or more anti-inflammatory agents in an amount of from about 0.01 to about 5% or in a range of from about 0.1 to about 2%, as discussed above for the additional medicaments, or in a range of from about 0.01 to about 1.0 wt. %.

The concentrated azalide antibiotic formulations may be formulated for administration via topical administration. The formulations can be administered to humans and a variety of non-human animals, the latter including but not limited to cows, sheep, horses, pigs, goats, rabbits, dogs, cats, and other mammals.

Any delivery technique and ocular dosage form that applies an azalide antibiotic to the external eye surface is included within the definition of "topically applying." Although the external surface of the eye is typically the outer layer of the conjunctiva, it is possible that the sclera, cornea, or other ocular tissue could be exposed such as by rotation of the eye or by surgical procedure, and thus be an external surface. For the purposes of this application, periocular tissues are defined as those tissues in contact with the lachrymal secretions, including the inner surface of the eye lid, the tissues of the orbit surrounding the eye, and the tissues and ducts of the lachrymal gland.

Generally a single application, such as one or two drops, provides a therapeutically effective concentration (i.e. one that retards or suppresses the infection) of the azalide antibiotic within a tissue. Indeed, although dependent on the amount and form of the ophthalmic composition, a single application will typically provide a therapeutically effective amount of the azalide antibiotic within a tissue for at least about 2-18 hours.

Azalide antibiotic formulations of this disclosure can be used to treat or prevent a variety of conditions associated with ocular infection. For example, conditions of the eyelids, including blepharitis, blepharconjunctivies, meibomianitis, acute or chronic hordeolum, chalazion, dacryocystitis, dacryoadenities, and acne rosacea; conditions of the conjunctiva, including conjunctivitis, ophthalmia neonatorum, and trachoma; conditions of the cornea, including corneal ulcers, superficial and interstitial keratitis, keratoconjunctivitis, foreign bodies, and post operative infections; and conditions of the anterior chamber and uvea, including endophthalmitis, infectious uveitis, and post operative infections, are a few of the tissues and conditions that can be treated by topical application of an azalide antibiotic. The prevention of infection includes pre-operative treatment prior to surgery as well as other suspected infectious conditions or contact. Examples of prophylaxis situations include treatment prior to surgical procedures such as blepharoplasty, removal of chalazia, tarsorrhaphy, procedures for the canualiculi and lacrimal drainage system and other operative procedures involving the lids and lacrimal apparatus; conjunctival surgery including removal of ptyregia, pingueculae and tumors, conjunctival transplantation, traumatic lesions such as cuts, burns and abrasions, and conjunctival flaps; corneal surgery including removal of foreign bodies, keratotomy, and corneal transplants; refractive surgery including photorefractive procedures; glaucoma surgery including filtering blebs; paracentesis of the anterior chamber; iridectomy; cataract surgery; retinal surgery; and procedures involving the extra-ocular muscles. The prevention of ophthalmia neonatorum is also envisaged. The formulation may be administered as an eye drop or in the blepharitis the drop may be rubbed into the eyelids.

About 30,000 to about 100,000 centipoise is an advantageous viscosity range for ophthalmic administration in ribbon form. Alternatively, a viscosity in the range of from about 1,000 to 30,000 centipoise is useful for a drop. In some embodiments, 1200 to about 20,000 centipoise, in other embodiments about 1500 to about 10,000 and other embodiments about 3000 centipoise.

A depot of the azalide antibiotic can be formed by several means within the eye. In one embodiment a depot for topical administration can be formed by including lightly crosslinked carboxyl containing polymers in the formulation, which causes the solution to undergo a rapid increase in viscosity upon a pH rise associated with administration to tissues such as those of the eye and surrounding region. In another embodiment, a depot of the azalide antibiotic can be formed by injection of a bolus of the antibiotic composition into an eye. In one embodiment, the method of ophthalmic administration the injection is intended to form a depot of material within the sclera, to accommodate extended release of the material to the surrounding tissues. Methods of intrascleral administration are discussed in U.S. patent application Ser. No. 09/127,920, filed Aug. 3, 1998 now U.S. Pat. No. 6,378, 526 and copending U.S. patent application Ser. No. 09/366, 072, filed Aug. 2, 1999, now U.S. Pat. No. 6,397,849. Other means of forming depot include the use of inserts loaded with a bolus of the drug to be delivered. Inserts placed under the eyelid have been used for example to deliver therapeutics to the ocular and periocular region.

In one embodiment where the concentrated azalide antibiotic formulation containing DuraSite® or other similar polyacrylic acid-type polymer at a pH of about 6 to about 6.8, or in another embodiment about 6.0 to about 6.5, or at a pH of about 6.2 to about 6.4, or in another embodiments about 6.25 to about 6.35, or about 6.3 is administered to the eye, the polymer will swell upon contact with tear fluid which has a higher pH. This gelation or increase in gelation leads to entrapment of the azalide antibiotic in the gel thereby extending the residence time of the composition in the eye if the antibiotic is in solution. If the azalide antibiotic is retained in the gel polymer matrix, the antibiotic is released slowly to the affected tissue over time. All these events eventually lead to increased patient comfort and increased azalide antibiotic contact time with the eye tissues, thereby increasing the extent of drug absorption and duration of action of the formulation in the eye. These antibiotics, display minimal degradation and relatively high solubility in aqueous formulations at the pre-administration pH, with the advantages of the gelling composition.

The viscous gels that result from fluid eye drops typically have residence times in the eye ranging from about 2 to about 4 hours, e.g., from about 2 to about 3 hours. The agents contained in these drug delivery systems will be released from the gels at rates that depend on such factors as the molecular weight of the drug, its ionization state, the extent of drug loading and the pH of the system, as well as on any drug delivery adjuvants, such as ion exchange resins compatible with the ocular surface, which may also be present.

An embodiment of the ophthalmic azalide formulations has about 2%, about 3%, about 4% and about 5% azithromycin with DuraSite® as the delivery vehicle. Such formulations are intended for the treatment of bacterial conjunctivitis. The formulations do not use a citrate buffer and may contain DuraSite® as the delivery vehicle. Moreover, in an embodiment ophthalmic formulations contain an anti-inflammatory agent such as dexamethasone. In addition to azithromycin content, the formulations have a pH of about 6 to about 7, and an osmolality of about 300 mOsm/kg. In some embodiments the osmolality is about 250 to about 330 mOsm/kg and in other embodiments 300 mOsm/kg. The formulations may have a viscosity of about 1000 to about 5000 cps. In some embodiments, the viscosity is about 1000 to about 2000 cps and in some embodiments the viscosity is about 1500 cps.

EXAMPLE 1

Ophthalmic Formulations Made at the 12 L Scale

In a first step, EDTA, sodium chloride and polycarbophil (Solution #1) are mixed for 30 minutes using an overhead mixer. The solution is then transferred to a stainless steel pressure can. The solution is transferred using pressure through a 100 mesh screen into the 12 L vessel. This solution is sterilized within the tank at 121.1° C. for 30 minutes. In the second step, sodium hydroxide is added aseptically through a 0.2 µm filter to the vessel containing Solution #1. The volume of sodium hydroxide required is based upon targeting a final batch pH of 6.3. The stainless steel pressure can and transfer line are then rinsed with house DI water. In a third step, mannitol, hydrochloric acid, azithromycin, benzalkonium chloride (BAC), and Poloxamer 407 (Solution #2) are mixed together. Hydrochloric acid is added to facilitate the dissolution of azithromycin. After all of the solid components in Solution #2 are fully dissolved, it is transferred aseptically into the 12 L vessel through a 0.2 µm filter. Alternatively, the sodium hydroxide may be added as the last step to insure a pH of 6.3 is achieved. The stainless steel pressure can and filter are then rinsed with DI water and the rinsate is added aseptically to the solution in the 12 L vessel. The rinse volume is determined by targeting a final batch volume of 12 liters. See Table 1.

As shown in FIG. 1, the formulation of the present disclosure in which a weak acid such as citric acid is not added, achieves greater stability over time versus a formulation in which citric acid is used.

EXAMPLE 2

Ophthalmic Formulations Made at the 12 L Scale with Chitosan

In a first step, EDTA, sodium chloride and polycarbophil (Solution #1) are mixed for 30 minutes using an overhead mixer. The solution is then transferred to a stainless steel pressure can. The solution is transferred using pressure through a 100 mesh screen into the 12 L vessel. This solution is sterilized within the tank at 121.1° C. for 30 minutes. In the second step, sodium hydroxide is added aseptically through a 0.2 µm filter to the vessel containing Solution #1. The volume of sodium hydroxide required is based upon targeting a final batch pH of 6.3. The stainless steel pressure can and transfer line are then rinsed with house DI water and added aseptically to the vessel through a 0.2 µm filter. In a third step, mannitol and benzalkonium chloride are dissolved in water and added aseptically to the vessel. Chitosan is dispersed in water and hydrochloric acid is added to achieve dissolution of the chitosan. This is then added aseptically into the vessel. Hydrochloric acid, azithromycin, and Poloxamer 407 (Solution #2) are mixed together. Hydrochloric acid is added to facilitate the dissolution of azithromycin. After all of the solid components in Solution #2 are fully dissolved, it is transferred aseptically into the 12 L vessel through a 0.2 µm filter. Alternatively, the sodium hydroxide may be added as the last step to insure a pH of 6.3 is achieved. The stainless steel pressure can and filter are then rinsed with DI water and the rinsate is added aseptically to the solution in the 12 L vessel. The rinse volume is determined by targeting a final batch volume of 12 liters.

TABLE 1

| Composition of Formulations Hydrochloric and Citric Acid | |
|---|---|
| Ingredients | Conc. (% w/w) |
| No Citrate Article # 1053-56-2 | |
| EDTA | 0.1 |
| NaCl | 0.25 |
| Polycarbophil | 0.95 |
| Mannitol | 1.5 |
| BAC | 0.01 |
| Na Citrate | 0 |
| Citric Acid | 0 |
| Poloxamer 407 | 0.2 |
| Azithromycin | 2 |
| HCl 2N | 2.8 |
| NaOH 2N | 5.45 |
| Water (qs) | 100 |
| Analyses @ T0: | |
| pH | 6.32 |
| Visc (cp) | 1341 |
| Osmo (mmOsm) | 297 |
| Citric Acid Control Article # 1053-56-1 | |
| EDTA | 0.1 |
| NaCl | 0.25 |
| Polycarbophil | 0.95 |
| Mannitol | 1 |
| BAC | 0.01 |
| Na Citrate | 0.14 |
| Citric Acid | 0.2 |
| Poloxamer 407 | 0.2 |
| Azithromycin | 2 |

TABLE 1-continued

Composition of Formulations Hydrochloric and Citric Acid

| Ingredients | Conc. (% w/w) |
|---|---|
| HCl 2N | 2.083 |
| NaOH 2N | 5.5 |
| Water (qs) | 100 |
| Analyses @ T0: | |
| pH | 6.29 |
| Visc (cp) | 1,266 |
| Osmo (mmOsm) | 266 |

TABLE 2

Composition of Formulation with Hydrochloric Acid and Chitosan

| Ingredients | Concentration (% w/w) |
|---|---|
| Sodium Edetate | 0.1 |
| Sodium Chloride | 0.25 |
| Polycarbophil | 0.95 |
| Chitosan | 0.025 |
| Hydrochloric Acid, 2N | 3.6 |
| Mannitol | 1 |
| Benzalkonium chloride | 0.01 |
| Poloxamer 407 | 0.2 |
| Azithromycin | 2 |
| Sodium Hydroxide, 2N | qs to pH 6.3 |
| Water | qs 100% |

It is to be understood that the present subject matter is capable of use in various combinations and environments other than the examples described and is capable of changes or modifications within the scope of the inventive concept as expressed herein. Thus, for example, those skilled in the art will recognize, or be able to ascertain, using no more than routine experimentation, numerous equivalents to the specific substances and procedures described herein. Such equivalents are considered to be within the scope of this disclosure. All references cited herein are incorporated by reference in their entirety for all purposes.

The invention claimed is:

1. A method of making a concentrated aqueous azithromycin formulation comprising from about 2% to 20% azithromycin, said method comprising the steps of:
   (a) preparing and sterilizing a first solution comprising a polymeric suspending agent the pH of which is adjusted with a strong base to form the first solution,
   (b) dissolving the azithromycin in an aqueous solution comprising an acid consisting essentially of a strong acid to form a second solution, and
   (c) adding the second solution comprising the strong acid to the first solution adjusted with the strong base,
   wherein the strong acid has a pKa less than about −1.74 and the method is carried out without addition or use of a weak acid.

2. The method of claim 1, wherein the strong acid is hydrochloric acid.

3. The method of claim 1 wherein the strong base is sodium hydroxide.

4. The method of claim 1, wherein the polymeric suspending agent is a lightly crosslinked carboxy-containing polymer.

5. The method of claim 1 wherein the aqueous azithromycin formulation further comprises an anti-inflammatory agent at a concentration of about 0.1% per weight of the total concentrated aqueous azithromycin formulation.

6. The method of claim 4, wherein the aqueous solution further comprises a chitosan having a molecular weight from about 500 kDa to about 5,000 kDa in an amount from about 0.01% to about 1.0%.

7. A method of treating or preventing conditions associated with ocular infection comprising the steps of:
   preparing a concentrated aqueous azithromycin formulation comprising from about 2% to 20% azithromycin, by sterilizing a first solution comprising a polymeric suspending agent the pH of which is adjusted with a strong base to form the first solution; dissolving the azithromycin in an aqueous solution comprising an acid consisting essentially of a strong acid to form a second solution; and adding the second solution comprising the strong acid to the first solution adjusted with the strong base, wherein the strong acid has a pKa less than about −1.74 and the method is carried out without addition or use of a weak acid; and applying the formulation to the eye and/or tissue surrounding the eye in an amount effective to treat the eye.

8. The method of claim 7, wherein the ocular infection is selected from the group consisting of: blepharitis, blepharconjunctivies, meibomianitis, acute or chronic hordeolum, chalazion, dacryocystitis, dacryoadenities, acne rosacea, bacterial conjunctivitis, ophthalmia neonatorum, trachoma, corneal ulcers, superficial and interstitial keratitis, keratoconjunctivitis, foreign bodies, post operative infections, endophthalmitis, and infectious uveitis.

9. The method of claim 7, wherein the formulation is applied to the eye and/or the tissue surrounding the eye prior or post to an ocular surgical procedure.

10. The method of claim 7, wherein the strong acid is hydrochloric acid.

11. A concentrated topical aqueous azalide antibiotic formulation comprising 2% to about 20% azithromycin and a polymeric suspending agent, said formulation made by dissolving azithromycin in a strong acid to form an azithromycin solution and then adding the azithromycin solution to a sterilized solution comprising the polymeric suspending agent, the pH of which is adjusted with a base, wherein the strong acid has a pKa less than about −1.74 and wherein the formulation is made in the absence of a weak acid.

12. The formulation of claim 11, wherein the strong acid is hydrochloric acid.

13. The formulation of claim 11 wherein the strong base is sodium hydroxide.

14. The formulation of claim 11, wherein the polymeric suspending agent is a lightly crosslinked carboxy-containing polymer.

15. The formulation of claim 14 wherein the polymeric suspending agent is Noveon AA-1.

16. The formulation of claim 14 further comprising an anti-inflammatory agent.

17. The formulation of claim 16 wherein the anti-inflammatory agent is dexamethasone.

18. The formulation of claim 17, wherein the dexamethasone has a concentration of about 0.1% per weight of the total concentrated aqueous azithromycin formulation.

19. The formulation of claim 14, wherein the aqueous solution further comprises a chitosan having a molecular weight from about 500 kDa to about 5,000 kDa in an amount from about 0.01% to about 1.0%.

20. The formulation of claim 14, wherein the aqueous solution further comprises a chitosan having a molecular weight from about 50 kDa to about 100 kDa in an amount from about 0.01% to about 1.0%.

21. The formulation of claim 11, wherein the weak acid is citric acid.

* * * * *

UNITED STATES PATENT AND TRADEMARK OFFICE
CERTIFICATE OF CORRECTION

PATENT NO. : 9,044,508 B2  Page 1 of 1
APPLICATION NO. : 13/843267
DATED : June 2, 2015
INVENTOR(S) : Bowman et al.

It is certified that error appears in the above-identified patent and that said Letters Patent is hereby corrected as shown below:

Title Page, Item (72) Inventor Name should read --Sui Yuen Eddie Hue-- rather than "Sui Yen Eddie Hue"

Signed and Sealed this
Thirty-first Day of May, 2016

Michelle K. Lee
*Director of the United States Patent and Trademark Office*